United States Patent [19]
Perkins

[11] Patent Number: 5,202,710
[45] Date of Patent: Apr. 13, 1993

[54] FIXATION CARD ATTACHMENT FOR RETINOSCOPE

[75] Inventor: David G. Perkins, Syracuse, N.Y.

[73] Assignee: Welch Allyn, Inc., Skaneateles Falls, N.Y.

[21] Appl. No.: 757,896

[22] Filed: Sep. 11, 1991

[51] Int. Cl.⁵ ............................................. A61B 3/10
[52] U.S. Cl. ................................. 351/211; 351/218; 351/216
[58] Field of Search ............... 351/205, 221, 218, 215, 351/211, 216, 214; 248/683; 359/903

[56] References Cited

U.S. PATENT DOCUMENTS 4,063,806 12/1977 LeVantine ..................... 351/213

Primary Examiner—Rodney B. Bovernick
Assistant Examiner—Hung Xuan Dang
Attorney, Agent, or Firm—Wall and Roehrig

[57] ABSTRACT

A fixation card attachment for an eye examination instrument that enables the card to be positioned in reference to the optical path of the instrument so that the patient undergoing examination must refocus his or her eye when reading indicia on the card. The card is secured to the instrument by use of a magnetic coupling. The magnetic coupling includes a permanent magnet encapsulated in the front face of the examination instrument and a magnetic strip provided on the back of the fixation card.

10 Claims, 2 Drawing Sheets

FIXATION CARD ATTACHMENT FOR RETINOSCOPE

BACKGROUND OF THE INVENTION

This invention relates to an instrument which is used by an examining physician or other medical healthcare worker to examine a patient's eye while the patient is observing indicia upon a fixation card.

When performing one type of eye examination, the examining physician observes the subject's eye through a retinscope. It is desirable at that time for the patient to move or focus his or her eye to correspond with the directions of the examiner in order to facilitate the examination of the appropriate optic structures and reflexes.

To test accommodation during near fixation, the patient must focus and refocus his or her eye. Reading indicia fixed upon a card, typically referred to as a fixation card, provides an effective means for so doing. Until now, however, the use of such a card in association with an instrument has been difficult.

One option was to have a free-standing card held at some appropriate reading distance by the examining physician with one hand while manipulating the instrument with the other hand. This, however, sometimes proves to be difficult and the card can be easily displaced, thus interfering with the examination.

Some retinoscopes are provided with external snap-on clips adapted to hold and position a fixation card in reference to the instrument. This solution, however, is not entirely satisfactory. Such clips are clumsy and awkward to use and are also subject to being bent or broken with handling and easily lost. In addition, while using such a clip, a card can become easily dislodged or misaligned. The addition of a clip to the exterior of a retinoscope makes the instrument bulky and thus more difficult to store or carry about in the pocket of a typical examination or laboratory jacket.

SUMMARY OF THE INVENTION

It is therefore a primary object of the present invention to provide an instrument which is used in conjunction with a fixation card having an a component that is integral with the instrument for supporting the card thereon in proper alignment during an eye examination.

Another object of this invention is to provide an instrument for examining an eye where the object indicia to be viewed by the person examined is held against the front face of the instrument by a magnetic coupling.

Another object of this invention is to provide a retinoscope wherein a fixation card is maintained at a fixed and steady position with respect to the optical path of the instrument.

Still another object of this invention is to provide a mechanism on a retinoscope for holding and positioning a card containing indicia, which mechanism is not subject to breakage.

Yet another object of this invention is to provide a mechanism for an eye examining instrument for holding and positioning a fixation card, which mechanism does not add to the external bulk of the instrument or adversely affect the aesthetics of the instrument.

These and other objects of the present invention are attained by an eye examination instrument to be used in conjunction with a fixation card. In the main embodiment of the invention, the fixation card is removably attached to the face of a retinoscope using a magnetic coupling. The face of the instrument is formed of a non-magnetic material in which a permanent magnet is encapsulated. The back of the fixation card is provided with a magnetic strip that is attracted to the magnet to hold the card securely against the instrument face. The card further contains an opening that is centered upon the optical axis of the instrument which enables the examining physician to examine the eye through the card. The card is placed at an angle with regard to the optical axis so that the patient must refocus his or her eye when reading indicia situated at different locations.

BRIEF DESCRIPTION OF THE DRAWINGS

For a better understanding of these and other objects of the present invention, reference is made to the detailed description of the invention which is to be read in conjunction with the following drawings, wherein.

DESCRIPTION OF THE INVENTION

Figure 1:
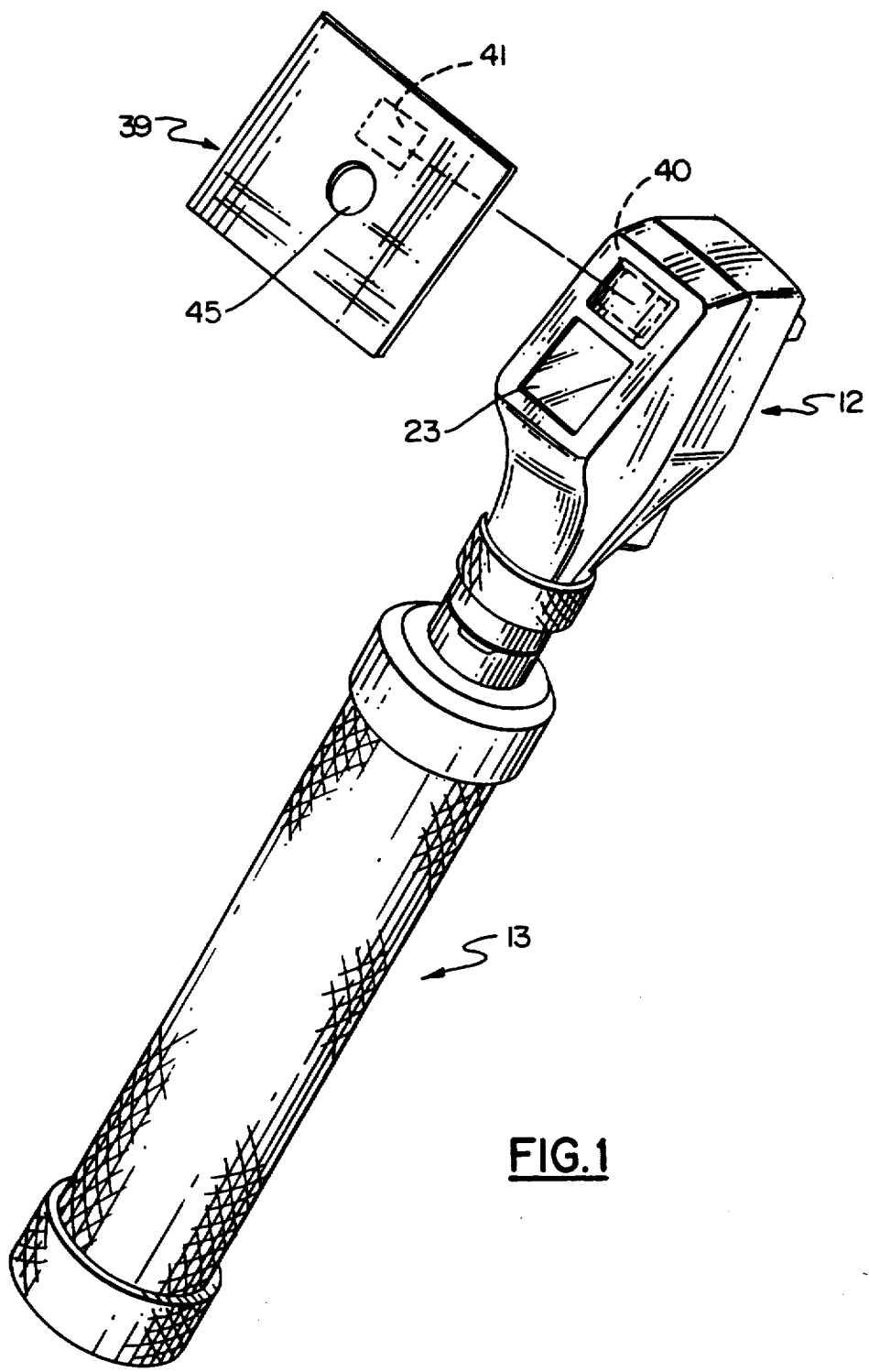
FIG. 1 is a perspective view of a retinoscope, embodying the teachings of the present invention.
Figure 2:
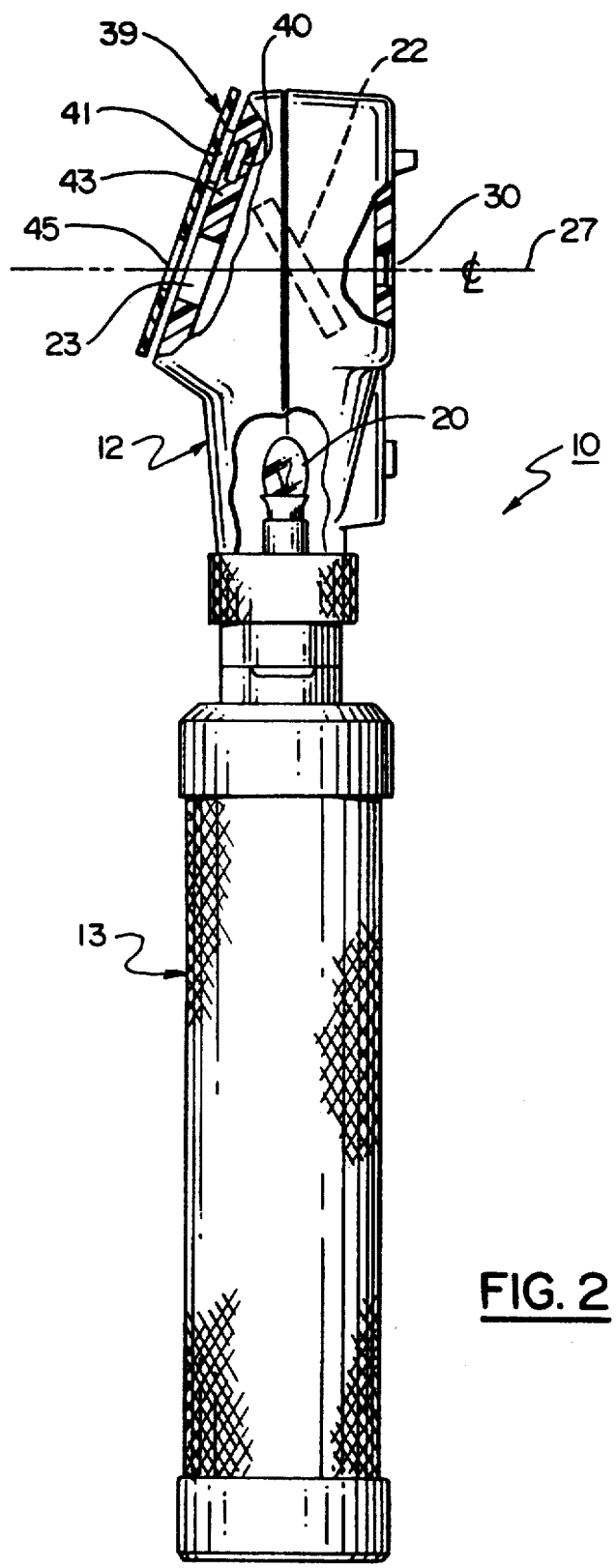
FIG. 2 is a side elevation with portions broken away showing a card angularly positioned with regard to the optical path of the instrument.

Referring now to the drawings, there is shown a medical diagnostic instrument, generally referenced 10, for examining a patient's eye which in this case is a retinoscope. This type of instrument is commercially available through Welch Allyn, Inc. of Skaneateles Falls, N.Y. The illustrated instrument includes an upper optical head 12 which is removably attached to a lower elongated battery handle 13 for providing power to the instrument, although other sources of power may be used without departing from the teachings of the present instrument. Basically, the handle contains a rechargeable battery and a recharging module that can be plugged into any conventional 120 volt outlet to recharge the battery. The positive terminal of the battery is located at the top of the handle and is arranged to make contact with an electrical terminal carried in the head section of the instrument when the head is operatively connected to the handle.

The head of the instrument includes a light source 20 which is preferably a high intensity halogen lamp. The lamp is arranged to direct a beam of light at a beam splitter 22 that redirects the light path through a front window 23 formed in the front face 25 of the head. The light is redirected along an optical path 27 toward the eye of a patient undergoing examination. A second smaller rear window 30 is furnished in the back wall 31 of the head with the rear window being centered upon the optical light path 27 of the instrument. The examining physician can thus view the illuminated region of the patient's eye directly along the light path of the instrument through the beam splitter. Although not shown, filters and/or polarizing lenses may be placed in the light path of the instrument to aid in the examination.

A fixation card 39 of suitable design and construction is mounted adjacent to the front face of the instrument head by means of a magnetic connection. A magnet 40 is mounted in the head directly over the front window. Preferably, the head is fabricated of a non-magnetic material such as plastic or the like and the magnet 40 is encapsulated in the wall material. The magnet 40 is situated so that the magnetic lines of flux extend outwardly beyond the front wall of the instrument head.

The fixation card has a thin magnetic strip 41 secured to its back face by which the card is attracted to and securely held against the front face of the optical head.

The size and shape of the magnetic strip 41 generally complements that of the magnet 40 so that the strip can be easily positioned on the magnet when it is introduced into the flux field. The bottom edge of the strip is located a given distance above the center of an opening 45 in the card which is equal to the distance that the bottom edge of the magnet is located above the optical light path 27 of the instrument. Accordingly, the opening in the card will be centered on the axis of the optical light path 27 when the card is magnetically coupled to the instrument head.

The front face of the instrument head is offset at an acute angle with respect to the optical light path 27 of the instrument. This forces the patient undergoing examination to refocus his or her eye as the eye is moved to read indicia located at various points on the fixation card.

While this invention has been explained with reference to the structure disclosed herein, it is not confined to the details set forth and this application is intended to cover any modifications and changes as may come within the scope of the following claims.

What is claimed is:

1. A diagnostic medical instrument for examining the eye of a patient that includes:
    a handle that is connected to an instrument head having a front wall and a rear wall,
    said head having a rear opening in the rear wall and a front opening in the front wall, said openings being centered on the same optical axis,
    a light source for illuminating a transparent reflector situated in said optical axis that the light passes through the front opening along said optical axis,
    a card containing indicia on its front face having an opening therein and magnetic means for connecting the back face of the card adjacent to the front wall of the instrument head with the opening in said card centered about said optical axis.

2. The instrument of claim 1 wherein said instrument head is formed of a non-magnetic material and said magnetic means includes a permanent magnet encapsulated in said head.

3. The instrument of claim 2 that further includes a magnetic strip attached to the back face of said card.

4. The instrument of claim 3 wherein the size and shape of the magnetic strip complements that of the magnet.

5. The instrument of claim 1 wherein the front wall of the instrument head forms an acute angle with the optical axis of the instrument.

6. The instrument of claim 1 wherein said handle contains battery means for providing power to the instrument.

7. An improved instrument for examining the eye of a patient having a handle connected to an instrument head, a light source and means for directing a beam of light along an optical axis to the patient's eye, the improvement comprising:
    a fixation card having indicia on the front face thereof and a centrally located hole formed in said card; and
    magnetic connecting means for removably attaching the card to the patient's side of the instrument with the opening of the hole centered upon the optical axis of said instrument.

8. The improvement according to claim 7 wherein magnetic connecting means includes a magnet and a magnetic strip, one of which is located on the card and the other of which is located on the instrument.

9. The improvement according to claim 8 wherein the magnet is encapsulated within a non-magnetic segment of the instrument.

10. The magnetic connecting means of claim 7 that further includes a first member mounted on the back of said card and a second member mounted on said instrument, said members interrelating when brought together to removably secure the card to the instrument with said hole centered upon the optical axis of the instrument.

* * * * *